(12) United States Patent
Shawer et al.

(10) Patent No.: US 8,173,169 B2
(45) Date of Patent: May 8, 2012

(54) FORMULATION AND PROCESS FOR THE PREPARATION OF MODAFINIL

(75) Inventors: Mohannad Shawer, Amman (JO); AlSayed AlArabi Sallam, Amman (JO); Dalia Jawhari, Amman (JO)

(73) Assignee: Hikma Pharmaceuticals, Amman (JO)

( * ) Notice: Subject to any disclaimer, the term of this patent is extended or adjusted under 35 U.S.C. 154(b) by 827 days.

(21) Appl. No.: 11/776,012

(22) Filed: Jul. 11, 2007

(65) Prior Publication Data

US 2007/0275057 A1 Nov. 29, 2007

(51) Int. Cl.
*A61K 9/16* (2006.01)
*A61K 9/20* (2006.01)
*A61K 9/48* (2006.01)

(52) U.S. Cl. .................. 424/489; 424/451; 424/464

(58) Field of Classification Search .................. None
See application file for complete search history.

(56) References Cited

U.S. PATENT DOCUMENTS

| | | | |
|---|---|---|---|
| 4,177,290 A | 12/1979 | Lafon | |
| 5,618,845 A | 4/1997 | Grebow et al. | |
| RE37,516 E | 1/2002 | Grebow et al. | |
| 6,489,363 B2 | 12/2002 | Jacobs | |
| 6,919,378 B2 | 7/2005 | Jacobs | |
| 7,115,281 B2 | 10/2006 | Singh | |
| 7,229,644 B2 | 6/2007 | Corvari | |
| 2002/0098240 A1 | 7/2002 | Jacobs et al. | |
| 2003/0022940 A1 | 1/2003 | Corvari | |
| 2004/0048931 A1 | 3/2004 | Heacock et al. | |
| 2004/0105891 A1 | 6/2004 | Bentolila et al. | |
| 2004/0116532 A1 | 6/2004 | Heacock et al. | |
| 2004/0121003 A1 | 6/2004 | Chickering et al. | |
| 2004/0167225 A1* | 8/2004 | Singh et al. .................. 514/618 |
| 2004/0170683 A1* | 9/2004 | Sherman ........................ 424/465 |
| 2004/0253308 A1 | 12/2004 | Ahmed et al. | |
| 2005/0070551 A1 | 3/2005 | Remenar | |
| 2005/0079138 A1 | 4/2005 | Chickering et al. | |
| 2005/0137264 A1 | 6/2005 | Patel et al. | |
| 2005/0249814 A1 | 11/2005 | Barbera et al. | |
| 2006/0024370 A1 | 2/2006 | Nguyen et al. | |
| 2006/0093678 A1 | 5/2006 | Chickering et al. | |
| 2007/0021510 A1 | 1/2007 | Hickey | |
| 2007/0048373 A1 | 3/2007 | Chastain | |
| 2007/0065517 A1 | 3/2007 | Heacock | |
| 2008/0031939 A1* | 2/2008 | Braude et al. ................. 424/456 |

FOREIGN PATENT DOCUMENTS

| | | |
|---|---|---|
| WO | WO/2004/010979 A1 | 2/2004 |
| WO | WO/2004/078161 A1 | 9/2004 |
| WO | WO/2005/004917 A2 | 1/2005 |
| WO | WO/2005/107719 A2 | 11/2005 |
| WO | WO/2006/086864 A1 | 8/2006 |

* cited by examiner

*Primary Examiner* — Susan Tran

(74) *Attorney, Agent, or Firm* — Sutherland Asbill & Brennan LLP

(57) ABSTRACT

The present invention provides pharmaceutical tablets comprising modafinil particles, processes for preparing such pharmaceutical tablets, and methods of treating a disease or disorder using the pharmaceutical tablet of the invention. In particular, the pharmaceutical tablet of the invention comprises modafinil particles and one or more pharmaceutically acceptable excipients, wherein the modafinil particles have a size distribution such that at least about 65% of the modafinil particles have a diameter greater than 220 microns and the tablet is bioequivalent to PROVIGIL®. The pharmaceutical tablet of the invention is prepared by a dry granulation method.

19 Claims, 2 Drawing Sheets

FORMULATION AND PROCESS FOR THE PREPARATION OF MODAFINIL

FIELD OF THE INVENTION

The present invention relates generally to modafinil dosage forms for oral administration and the preparation of modafinil dosage forms. In particular, the present invention relates to a pharmaceutical tablet comprising coarse modafinil particles, still exhibiting relatively rapid dissolution and processes for preparing such pharmaceutical tablets.

BACKGROUND OF THE INVENTION

Modafinil is a drug generally used to treat excessive sleepiness caused by narcolepsy, obstructive sleep apnea/hypopnea syndrome (OSAHS) and shift work sleep disorder (SWSD). It is often described as a "wakefulness promoting agent" and is also prescribed for improving memory and mood. The drug and its uses were disclosed in already expired U.S. Pat. No. 4,177,290. Modafinil is marketed in the United States under the trade name PROVIGIL® in tablets comprising 100 mg and 200 mg modafinil.

The benzhydrylsulfinyl acetamide structure of modafinil makes it generally insoluble in water. One way to address the problem of insolubility is reducing the drug's particle size to increase the effective exposed surface area. U.S. Pat. No. RE 37,516 discloses improving solubility by a method of size reduction and a pharmaceutical composition that has at least about 95% of the modafinil particles having a diameter of less than about 200 μm and having a median size smaller than about 60 μm.

Another way to improve solubility includes surface treatment of drug particles using hydrophilic agents as disclosed in US application No. 20040253308 and WO application No. 2005004917.

Yet another way to improve solubility is disclosed in U.S. Pat. No. 7,115,281 which uses modafinil particles having bimodal size distributions. The size distribution is such that a proportion of the particles is smaller than about 41 um and a second proportion is greater than about 220 um.

Prior art approaches have focused so far on predominantly reducing particle size of modafinil.

There is an ongoing need to optimize the formulation and the methods used to prepare solid dosage forms of modafinil. Therefore, it would be desirable to provide a pharmaceutical formulation comprising modafinil particles having larger diameters made by a commercially feasible process, which is bioequivalent to PROVIGIL®.

SUMMARY OF THE INVENTION

The invention provides oral pharmaceutical compositions comprising coarse modafinil particles, which exhibit comparable in-vivo plasma concentrations with Provigil®

The invention provides an oral pharmaceutical composition comprising modafinil particles and one or more pharmaceutically acceptable excipients, wherein the modafinil particles have a size distribution such that at least about 65% of the modafinil particles have a diameter greater than about 220 microns. In one preferred embodiment, the pharmaceutical composition of the invention is prepared by a dry granulation method.

The invention further provides a process for preparing a pharmaceutical composition comprising modafinil and one or more pharmaceutically acceptable excipients, wherein the process comprises the steps of: (i) mixing of suitable excipients and active ingredient; ii) dry granulating and granule sizing; iii) final blending; and iv) compressing into tablets.

Also provided by the present invention is a method of treating a disease or disorder in a subject in need thereof comprising administrating to the subject a therapeutically effective amount of the pharmaceutical composition of the invention.

DETAILED DESCRIPTION OF THE INVENTION

Figure 1:
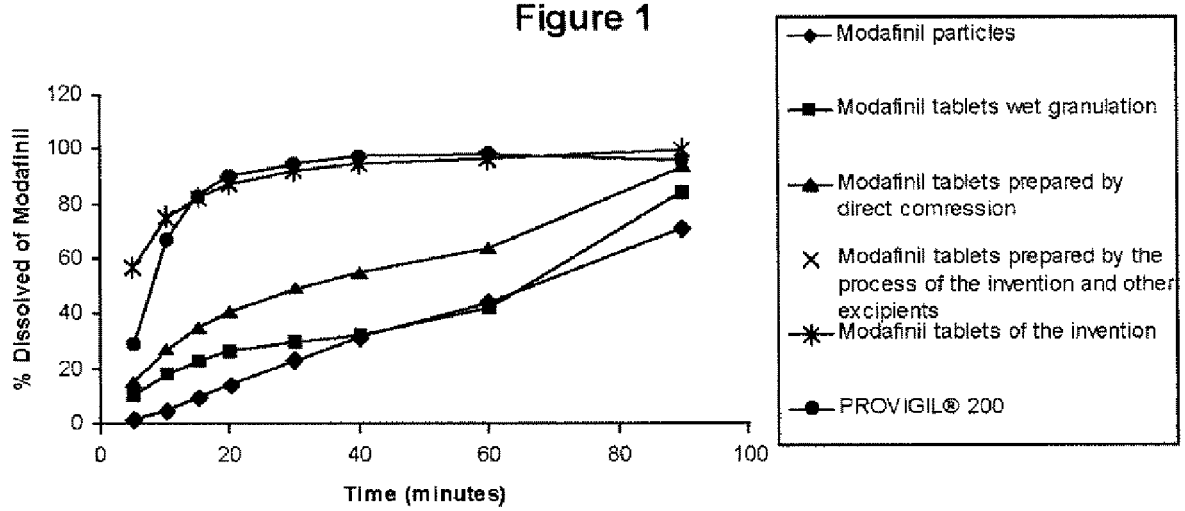
FIG. 1 Comparison between dissolution profiles of modafinil tablets prepared by the dry granulation method of the invention with that of modafinil tablet formulations prepared by other processes.
Figure 2:
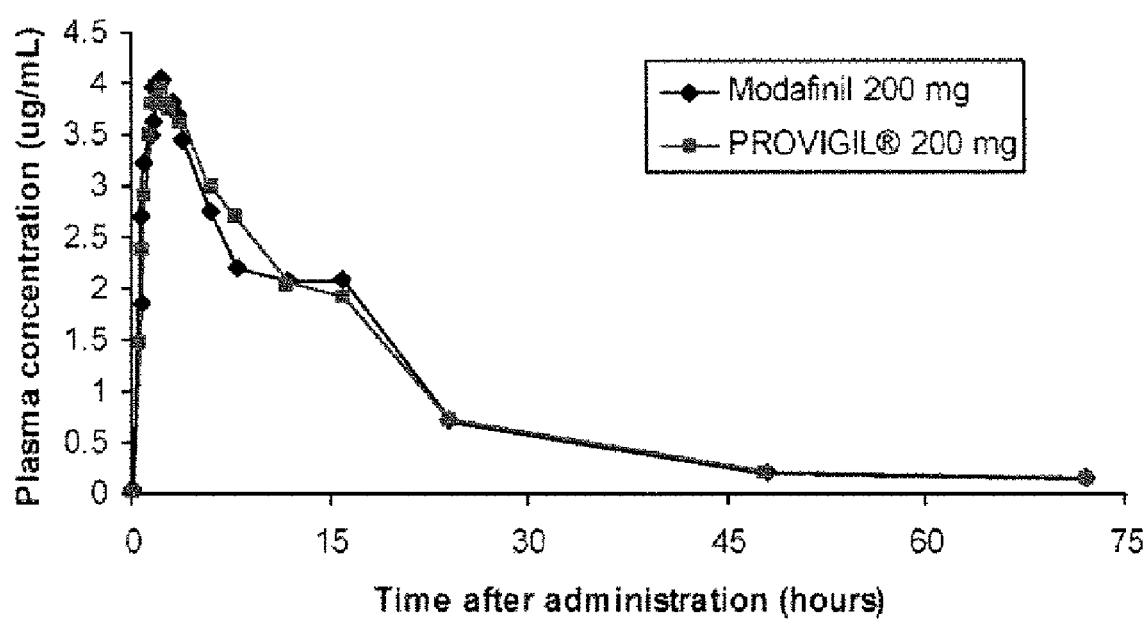
FIG. 2 Comparison between plasma concentrations of modafinil tablets containing 200 mg prepared by the dry granulation method of the invention and PROVIGIL® 200.

The present invention results from the discovery that modafinil particles prepared by a dry granulation method have an improved effective dissolution rate without the necessity to prepare a majority of particles in sizes below 200 μm.

"Particle" as used herein, refers to an aggregated physical unit of the modafinil compound, i.e. a piece or a grain of modafinil. As used herein, the term "diameter" is a volumetric measurement based on the presumed spherical shape of modafinil particles. As used herein, "about" means plus or minus approximately ten percent of the indicated value.

Modafinil particles of the invention may be in the form of the base or any pharmaceutically acceptable salt thereof.

As used herein, the term "slug" refers to a compact of the drug alone or mixed with excipients.

The invention provides a pharmaceutical composition comprising modafinil particles and one or more pharmaceutically acceptable excipients, a process for preparing the pharmaceutical composition, and a method of treating a disease or disorder using the pharmaceutical composition. In one preferred embodiment, the pharmaceutical tablet comprises the modafinil particles having a size distribution such that at least about 65% of the modafinil particles have a diameter greater than 220 microns.

In accordance with the invention disclosed herein, it is preferable that at least about 65% of the cumulative total (percent cumulative) of modafinil particles have particle sizes greater than 220 microns.

As used herein, the term "modafinil" refers to modafinil, its racemic mixtures, individual enantiomers, acid addition salts, such as a metabolic acid of modafinil, benzhydrylsulfinylacetic acids, and its sulfone forms, hydroxylated forms, polymorphic forms, analogs, derivatives and prodrugs thereof. Prodrugs are known in the art as compounds that are converted to modafinil in the body of a subject.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

It is noted that the size of modafinil particles may be determined by any of several conventional methods. Methods useful for analyzing particle size include, but are not limited to, laser diffraction particle size analysis, mechanical sieving, optical microscopy, ultracentrifugation, sedimentation, air permeability, electron microscopy, scanning electron microscopy and Coulter Counter techniques. For a general review of methods for determining particle size, see Martin et al., Physical Pharmacy, 3rd Ed., Lea & Febiger, Philadelphia (1983). See also O'Conner in Remington's Pharmaceutical Sciences, Section IX.

In certain embodiments, the pharmaceutical composition comprises one or more pharmaceutically acceptable excipients. In a preferred embodiment, the pharmaceutical composition comprises modafinil particles, one or more binders, diluents, disintegrants, surfactants, lubricants, glidants, and coloring agents.

The excipients are selected to enhance dissolution of modafinil particles, ensure the delivery of a consistent amount of modafinil in the pharmaceutical composition and to optimize the cost, ease and reliability of the manufacturing process.

All excipients must be inert, organoleptically acceptable, and compatible with modafinil. Examples of excipients include, but are not limited to, diluents, disintegrants, lubricants, glidants, binders, fillers, emulsifiers, electrolytes, wetting agents, solubilizers, surfactants, colors, pigments and anti-caking agents. A combination of excipients may be also used. Preferably, the excipients meet the standards of the National Formulary ("NF") or United States Pharmacopoeia ("USP").

In yet another preferred embodiment, one or more pharmaceutically acceptable excipients of the pharmaceutical composition are dissolution enhancing which improve the dissolution of modafinil particles.

In yet another preferred embodiment the excipients are particularly chosen to enhance fracture of the modafinil particles. Therefore, they are predominantly materials that consolidate by elastic deformation.

In yet another embodiment, the excipients are added stepwise to the first, second and final blends to further enhance the dissolution of modafinil.

Diluents are typically added to increase tablet weight. The most common diluent is lactose, which exists in two isomeric forms, alpha-lactose or beta-lactose, and can be either crystalline or amorphous. Various types of lactose include spray dried lactose monohydrate, alpha-lactose monohydrate, anhydrous alpha-lactose, anhydrous beta-lactose, and agglomerated lactose. Other diluents include sugars, dextrose and polyols such as mannitol, sorbitol and xylitol. Organic acids such as tartaric acid may also be used. Inorganic salts, such as dibasic calcium phosphate, tribasic calcium phosphate, and calcium sulfate. A preferred diluent is lactose monohydrate.

In a preferred embodiment of the invention, the total disintegrant, diluent and surfactant quantities per tablet are added in two or more portions to the modafinil dry granulation. For example, it is preferable that about 20% of lactose is mixed with modafinil for the first slug and about 30% added to the sized granules of the first slug before proceeding with the second slugging step. The remaining 50% of lactose is added to the final blend prior to tablet compression. For the disintegrants, greater than 50% is added in the first slug with remaining quantities added in subsequent steps. For sodium lauryl sulphate, about 15% is added to the slugs with the remainder added to the final blend prior to tablet compression.

Disintegrants may include starch, starch derivatives and cross-linked polymers such as polyvinyl pyrrolidone or crospovidone. Starches include native starches obtained from wheat, corn, rice and potatoes. Other starches include pregelatinized starch and sodium starch glycolate. Disintegrants are added to tablet formulations to facilitate dissolution of the active pharmaceutical ingredients and enhance bioavailability by breaking the tablets into particles of the active pharmaceutical ingredient and excipients. Starch and starch derivatives, including cross-linked sodium salt of a carboxymethyl ether of starch or starch derivatives are useful disintegrants. A preferred disintegrant is crospovidone.

Binders are included to agglomerate the active pharmaceutical ingredient and the other excipients. A binder also improves powder flow and compactibility. Binders include cellulose derivatives such as microcrystalline cellulose, methylcellulose, carboxymethylcellulose sodium, hydroxypropyl methylcellulose, hydroxyethyl cellulose, and hydroxypropyl cellulose. Other binders include polyvidone, polyvinyl pyrrolidone, gelatin, natural gums, starch paste, pregelatinized starch, sucrose, corn syrup, polyethylene glycols, and sodium alginate, ammonium calcium alginate and polyethylene glycols. A preferred binder is hydroxypropyl cellulose.

Lubricants are used to prevent sticking of the tablet and to reduce friction during the compression stages in tablet formulation. Lubricants typically include vegetable oils, mineral oils, polyethylene glycols (such as PEG-4000 and PEG-6000), salts of stearic acid (such as calcium stearate, magnesium stearate, and sodium stearyl fumarate), mineral salts (such as talc), organic salts (such as sodium benzoate, sodium acetate, and sodium oleate) and polyvinyl alcohols. A preferred lubricant is sodium stearyl fumarate.

Glidants are added to improve flow, generally by reducing inter-particle friction in the formulation. Commonly used glidants include alkali stearates (such as magnesium stearate or calcium stearate), silicate salts (such as magnesium silicate, magnesium trisilicate, magnesium silicate anhydrous, calcium silicate), starches, mineral salts (such as talc), and colloidal silicon dioxide.

Further, surfactants, such as ionic, non-ionic and/or bile salt surfactants, can also be included in the pharmaceutical formulation. Anionic surfactants include, but are not limited to, sodium lauryl sulphate, sodium laurate, dialkyl sodium sulfosuccinates, sodium stearate, potassium stearate, and sodium oleate. Preferred anionic surfactant is sodium lauryl sulphate. Non-ionic surfactants include, but are not limited to, one or more of polyoxyethylene sorbitan fatty acid esters, fatty alcohols, glyceryl esters, fatty acid esters of fatty alcohols and alcohols. Bile salt surfactants include, but are not limited to deoxycholic acid, sodium deoxycholate, cholic acid, and sodium taurocholate.

Percentage weight of modafinil and of one or more pharmaceutically acceptable excipients in the pharmaceutical composition can vary. In certain embodiments, modafinil particles may comprise from about 10-80% by weight of the tablet, about 15-65% by weight of the tablet, or about 20-50% by weight of the tablet. In a preferred embodiment, the tablet contains about 20-40% of modafinil particles by weight of the tablet.

The total weight of modafinil and one or more pharmaceutically acceptable excipients of the pharmaceutical tablet can vary as well. In certain embodiments, the total weight of modafinil in the pharmaceutical tablet containing one or more pharmaceutically acceptable excipients can be about 10 milligrams to about 800 milligrams, preferably between about 50 milligrams to about 400 milligrams, and most preferably between about 100 milligrams to about 200 milligrams. In a preferred embodiment, the tablet contains 100 milligrams or 200 milligrams of modafinil.

In certain preferred embodiments, the pharmaceutical tablet of the invention comprises modafinil particles, hydroxypropylcellulose, lactose monohydrate, pregelatinized starch, crospovidone, low substituted hydroxylpropyl cellulose, sodium lauryl sulphate, sodium stearyl fumarate, talc and combinations thereof.

In a preferred embodiment, the pharmaceutical composition may be prepared by a dry granulation method. The dry granulation method of the invention comprises the steps of: (i) blending modafinil particles and one or more pharmaceutically acceptable excipients to form a first mixture; (ii) subjecting the first mixture of step (i) to compression to form a slug; (iii) sizing the slug of step (ii) by passing through a 1 mm screen; (iv) blending the resulting granules of step (iii) and one or more pharmaceutically acceptable excipients to form a second mixture; (v) subjecting the second mixture of step (iv) to compression to form a second slug; (vi) sizing the slug of step (v) by passing through a 1 mm screen; (vii) blending the resulting granules of step (vi) with one or more pharmaceutically acceptable excipients; and (viii) compressing the mixture of step (vii) into a tablet.

In step (i), modafinil particles with one or more pharmaceutically acceptable excipients are blended to form a first mixture. Preferably, modafinil particles are thoroughly dry blended with at least one glidant, diluent, binder and disintegrant to form a uniform dry mixture. Blenders appropriate for dry blending include twin shell blender, double cone blenders, V-blenders or bin-blenders. High-speed, high-shear mixers may also be used.

In step (ii), the resulting dry mixture is compressed to form slugs in the tabletting machine. The compression machinery typically contains two steel punches within a steel die cavity. The slug is formed when pressure is exerted on the dry blend mixture by the punches in the cavity. Tabletting machines include single-punch machines, rotary tablet machines, gravity feed or force feed assisted machines. This compression process is generally known as "slugging" and the compact made in the process (typically about 25 mm diameter by about 10-15 mm thick) is termed a "slug," however, the particular size of the slug is not a limiting factor for the present invention.

In step (iii), the first slug is sized using an oscillator granulator or similar equipment used in the art for this purpose to produce granules and sieved to separate the desired size fraction. Preferably, the slugs of the invention are sized by passing through a 1 mm mesh.

In step (iv), the granules are further blended with additional one or more pharmaceutically acceptable excipients to form a second mixture. Preferably, the granules are thoroughly dry blended with at least one glidant, diluent, binder and disintegrant, to form a uniform dry mixture.

In step (v), the resulting dry mixture is compressed to form a second slug in the tabletting machine.

The second slug is sized using an oscillator granulator, or similar equipment used in the art for this purpose, fitted with a 1 mm mesh to produce granules. The granules from the second slug may be blended with an extragranular portion of one or more pharmaceutically acceptable excipients in step (vii). Then, the final blend is compressed into a final tablet in step (viii).

In one embodiment, the first slug of the pharmaceutical tablet of the invention may comprise modafinil, hydroxypropylcellulose, lactose monohydrate, preglatinized starch, talc, sodium lauryl sulphate, tartaric acid and the combinations thereof. In another embodiment, the second slug of the pharmaceutical tablet of the invention may comprise modafinil, lactose monohydrate, talc, sodium lauryl sulphate, crospovidone and the combinations thereof. Lubricants may be added in the final step to the granules obtained from the second slugging process.

The pharmaceutical tablet of the invention may be characterized by having bioequivalence equal to a tablet containing an equivalent amount of modafinil (PROVIGIL®) identified by the Food and Drug Administration as the reference listed drug. As used herein, the term "bioequivalent" or "bioequivalence" is defined in accordance with Approved Drug Products with Therapeutic Equivalence Evaluations, 22nd Edition, which is published by the U.S. Department of Health and Human Services.

Bioequivalence can generally be defined as the absence of significant difference in the rate and extent to which the active ingredient or active moiety in pharmaceutical equivalents or pharmaceutical alternatives becomes available at the site of drug action when administered at the same molar dose under similar conditions in an appropriately designed study. Bioequivalence of different formulations of the same drug substance involves equivalence with respect to the rate and extent of drug absorption. The extent and rate of absorption of the test formulation is compared to a reference formulation in order to determine whether the two formulations are bioequivalent. The standard bioequivalence study is conducted in crossover fashion by extensive testing which includes administering single doses of the test and reference drugs to a number of volunteers, usually 12 to 24 healthy normal adults, and then measuring the blood or plasma levels of the drug over time.

The pharmacokinetic characteristics of the concentration-time curve, such as the maximum observed plasma concentration ($C_{max}$), the time to reach $C_{max}$, and the area under the plasma concentration versus time curve (AUC), are examined by statistical procedures which are well-established in the field of pharmacokinetics. Two formulations whose rate and extent of absorption differ by −20%/+25% or less are generally considered to be bioequivalent. Detailed guidelines for establishing the bioequivalence of a test formulation with a reference have been published by the FDA Office of Generic Drugs, Division of Bioequivalence.

The method used to prepare the pharmaceutical tablets of the invention enhances the dissolution of modafinil by means of a conventional dry granulation method. Dry granulation is not a method conventionally used in the pharmaceutical arts to increase the solubility of large insoluble particles. This is because the intent of the dry granulation method is to form larger aggregates from primary particles which is expected to further decrease solubility. Therefore it is surprising that the method of the invention based on dry granulation is able to increase the solubility of large modafinil particles in the size range from at least about 65% to 80% greater than 220 μm.

It will be understood that the processes described herein have general applicability for preparing poorly soluble drugs having crystals with similar propensity to fracture upon compression. The invention provides that other compounds may benefit from increased solubility as a result of being prepared by the dry granulation method of the present invention.

The dry granulation methods disclosed herein are useful for preparing pharmaceutical tablets including, but not limited to, molded tablets, chewable tablets, sugar-coated tablets, multi-pressed tablets. Bi-layer tablets, enteric-coated tablet, film-coated tablets, pellets, pills, effervescent tablets, controlled-release tablets and immediate release tablets. In one embodiment, the pharmaceutical tablet of the invention may optionally be coated with one or more functional and/or non-functional coatings as desired.

The invention provides a method of treating a disease or disorder in a subject in need thereof comprising administrating to the subject a therapeutically effective amount of the pharmaceutical tablet of the invention. In one embodiment, the pharmaceutical compositions are useful to treat sleepiness, such as excessive daytime sleepiness associated with narcolepsy, or sleepiness associated with sleep apneas (obstructive sleep apnea/hypopnea syndrome (OSAHS) and shift work sleep disorder (SWSD)), tiredness, Parkinson's disease, cerebral ischemia, stroke, sleep apneas, eating disorders, attention deficit hyperactivity disorder, cognitive dysfunction or fatigue, such as fatigue resulting from multiple sclerosis ("MS fatigue"); and for promotion of wakefulness, stimulation of appetite, or stimulation of weight gain.

As used herein, the term an "effective amount" is an amount of modafinil that is effective to treat a somnolent or somnolescent state in which an amount of modafinil can reduce or eliminate the symptoms of a somnolescent state. An effective amount of a pharmaceutical composition of the invention is useful for enhancing alertness or increasing regularity of sleep rhythms and will vary according to the condition of the patient.

These and many other variations and embodiments of the invention will be apparent to one of skill in the art upon a review of the appended description and examples.

Example 1

As is appreciated by those in the art, different measurement instruments may provide different measurements of the same particles. Therefore, the result values for the sizes obtained may not be exactly replicated between the different methods although it is expected that they will be relatively comparable. Applicants have therefore performed modafinil particle size analysis using a Malvern Mastersizer 2000 (Worcestershire, UK), and a Coulter Counter (Hiac/Royco instruments, USA) and mechanical sieving methods.

Malvern Mastersizer utilizes the principle of laser diffraction particle sizing. The principle involved is that during the laser diffraction measurement, particles are passed through a focused laser beam and these particles scatter light at an angle that is inversely proportional to their size. The angular intensity of the scattered light is then measured by a series of photosensitive detectors and the map of scattering intensity versus angle is the primary source of information used to calculate the particle size.

In using the Coulter Counter, particles suspended in a weak electrolyte solution are drawn through a small aperture, separating two electrodes between which an electric current flows. The voltage applied across the aperture creates a "sensing zone". As particles pass through the aperture, they displace their own volume of electrolyte, momentarily increasing the impedance of the aperture. This change in impedance produces a pulse that is digitally processed in real time. The Coulter Principle states that the pulse is directly proportional to the tri-dimensional volume of the particle that produced it. Analyzing these pulses enables a size distribution to be acquired and displayed in volume ($\mu m^3$ or fL) and diameter ($\mu m$). Sieve sizing is one of the oldest methods used to determine particle size distributions. Samples of known weight are placed on the largest sieve in a stack of sieves of decreasing size. Upon shaking, sample fractions are caught on the respective sieve corresponding to the size of the particles.

Particle size measurements using the Hiac/Royco were generated on Modafinil particles of the present invention suspended in saturated water. For Malvern laser sizing, Modafinil particles can either be suspended in sunflower oil or sized in the dry form. Particle diameters obtained are shown in Table 1.

TABLE 1

Particle Size Analysis (Malvern Mastersizer 2000) for Modafinil B# 62605008s.
Particle Size Distribution of Modafinil Particles (% Undersize)

| Trial | d (0.1) | D (0.35) | d (0.5) | d (0.85) | d (0.9) | d (0.95) |
|---|---|---|---|---|---|---|
| 1 | 172.45 | 273.94 | 328.58 | 510.24 | 561.92 | 633.06 |
| 2 | 159.38 | 266.93 | 322.53 | 507.09 | 558.30 | 632.46 |
| 3 | 152.26 | 261.04 | 316.66 | 502.79 | 552.16 | 629.94 |
| Average | 161.37 | 267.3 | 322.59 | 506.71 | 557.46 | 631.82 |
| SD | 10.239 | 6.45 | 5.958 | 3.739 | 4.935 | 1.655 |
| RSD | 6.345 | 2.41 | 1.847 | 0.738 | 0.885 | 0.262 |

Table 2 summarizes particle size distribution of Modafinil of the present invention measured by sieve size analysis.

TABLE 2

Sieve Analysis Data for Modafinil B# 62605008s

| Particle size range (μm) | % Oversize |
|---|---|
| >800 | 0.00 |
| 600-800 | 0.25 |
| 500-600 | 5.26 |
| 425-500 | 12.78 |
| 355-425 | 17.04 |
| 250-355 | 52.88 |
| 180-250 | 7.02 |
| 150-180 | 1.25 |
| 0-150 | 3.51 |

Tables 1 and 2 summarize the particle size distribution of modafinil particles B#62605008s obtained by two different sizing methods. Values are reported in microns. The term d (0.1) denotes the diameter of the largest particle found in 10% of the particles sorted in increasing order. The other four terms refer to the diameter of the largest particle found in each 50%, 85%, 90% and 95% of the particles. The term SD denotes the standard deviation and is a measure of the spread of its values and the term RSD refers to the absolute value of the coefficient variation expressed as a percentage. In Table 2 the percentage by weight of particles retained on each mesh cut is reported. The data reported in Tables 1 & 2 shows that at least 65% of the particles is greater than 220 um.

In conclusion, the particle size data generated for Modafinil particles by two different sizing methods confirm that at least 65% of particles are greater than 220 um.

Example 2

Table 3 below compares between different dissolution profiles to show that Modafinil tablets made by the process of the invention using the dissolution enhancing excipients of the invention (column 5) is significantly better than other formulation approaches and is comparable to the dissolution profile of the reference listed drug PROVIGIL® 200 (column 6). To further demonstrate the superiority of the formulation of the invention, we have compared between the dissolution profiles of Modafinil particles alone in column 1, a wet granulation formulation in column 2, and a direct compression formulation in column 3. All three profiles are significantly slower than that of PROVIGIL® 200. The choice of excipient is also shown to have a significant influence on the dissolution profiles. As shown in column 4, failure to add the excipients in portions to the process of the invention resulted in a slower dissolution profile than that obtained for the tablets of the invention shown in column 5.

TABLE 3

Summary of Dissolution Rates of Modafinil
(with Excipients or without Excipients)
Prepared by Different Formulation Processes

| Time (mins) | 1 Modafinil particles | 2 Modafinil tablets wet granulation | 3 Modafinil tablets prepared by direct comression | 4 Modafinil tablets prepared by the process of the invention, excipients added in final blend | 5 Modafinil Tablets of the invention | 6 PROVIGIL ® 200 |
|---|---|---|---|---|---|---|
| | | | % Modafinil Dissolved | | | |
| 5 | 1.80 | 10.58 | 15.30 | 23.9 | 56.63 | 28.7 |
| 10 | 5.19 | 18.09 | 26.37 | 35.0 | 75.47 | 66.8 |
| 15 | 9.73 | 23.17 | 34.97 | 40.8 | 84.15 | 83.5 |
| 20 | 14.31 | 26.73 | 40.79 | 44.7 | 89.41 | 90.5 |
| 30 | 23.19 | 29.5 | 49.06 | 49.5 | 94.25 | 94.9 |
| 40 | 31.25 | 32.33 | 54.83 | 53.5 | 96.43 | 97.0 |
| 60 | 44.09 | 42.25 | 63.80 | 59.0 | 98.85 | 97.7 |
| 90 | 71.42 | 84.20 | 93.38 | 83.8 | 101.50 | 95.8 |

Example 3

Table 4 shows a way of formulating modafinil tablets of the invention. The excipients were selected and added in sequential order to result in tablets with comparable dissolution with PROVIGIL®. Modafinil with desired particle size is mixed with low substituted hydroxypropyl cellulose and pregelatinized starch.

TABLE 4

Modafinil tablet formulation with dissolution enhancing excipients

| Name | Amount (mg\tab) |
|---|---|
| Modafinil | 200 |
| Lactose monohydrate | 251.5 |
| Pregelatinized starch | 100 |
| Crospovidone | 80 |
| Low substituted hydroxypropyl cellulose | 25 |
| Sodium lauryl sulphate | 9.375 |
| Na stearyl fumarate | 6.62 |
| Talc | 9.375 |
| Total weight | 682 |

Portions of lactose, sodium lauryl sulphate and talc ranging from 10-50% to form the first slug (as shown in Table 5 below). The sized granules (by passing through 1 mm screen) from first slug are further mixed with second portions of lactose, sodium lauryl sulphate, talc and crospovidone to form the second slug. The sized granules (by passing through a 1 mm screen) from the second slug are mixed with second portions of lactose, sodium lauryl sulphate, talc and crospovidone ranging from 15-50% and compressed into final Modafinil tablets.

TABLE 5

Formulation Composition of Modafinil

| Components | Weight per/tablet (mg) |
|---|---|
| First Slug | |
| Modafinil | 200 |
| Low substituted hydroxypropylcellulose | 25 |
| Lactose monohydrate | 40 |
| Pregelatinized starch | 100 |
| Talc | 1.33 |
| Na lauryl sulphate | 1.33 |
| Second Slug | |
| Crospovidone | 20 |
| Talc | 1.43 |
| Na lauryl sulphate | 1.43 |
| Lactose monohydrate | 61.5 |
| Extra-granular excipients | |
| Crospovidone | 60 |
| Lactose monohydrate | 150 |
| Na lauryl sulphate | 6.62 |
| Talc | 6.62 |
| Na stearyl fumarate | 6.62 |

Example 5

Bioequivalence Comparison of Modafinil Tablets of the Invention with PROVIGIL® 200

The area under curve (AUC) and the maximum plasma concentration of Modafinil obtained in vivo ($C_{max}$) were determined for Modafinil tablets of the invention and PROVIGIL® 200. The average blood levels of 12 volunteers in ug/mL are given in Table 6.

TABLE 6

Comparative blood levels results (n = 12)

| Time after administration (hours) | Modafinil 200 mg | | PROVIGIL ® 200 mg | |
|---|---|---|---|---|
| | Average | Standard Deviation | Average | Standard Deviation |
| 00.0 | 0.0 | 0.0 | 0.0 | 0.0 |
| 0.5 | 1.85 | 0.92 | 1.47 | 1.26 |
| 0.75 | 2.69 | 1.15 | 2.37 | 1.84 |
| 1.0 | 3.22 | 1.35 | 2.89 | 1.63 |
| 1.50 | 3.50 | 1.49 | 3.49 | 1.59 |

TABLE 6-continued

Comparative blood levels results (n = 12)

| Time after administration (hours) | Modafinil 200 mg | | PROVIGIL ® 200 mg | |
|---|---|---|---|---|
| | Average | Standard Deviation | Average | Standard Deviation |
| 1.75 | 3.66 | 1.35 | 3.80 | 1.65 |
| 2.00 | 3.92 | 1.37 | 3.82 | 1.52 |
| 2.25 | 4.04 | 1.32 | 3.92 | 1.30 |
| 2.50 | 4.02 | 1.12 | 3.98 | 1.28 |
| 2.75 | 3.76 | 1.00 | 3.80 | 1.28 |
| 3.00 | 3.82 | 1.06 | 3.78 | 1.17 |
| 3.50 | 3.69 | 0.76 | 3.62 | 0.82 |
| 4.00 | 3.45 | 1.00 | 3.63 | 0.89 |
| 6.00 | 2.74 | 0.54 | 2.97 | 0.75 |
| 8.00 | 2.21 | 0.57 | 2.69 | 1.49 |
| 12.00 | 2.07 | 1.64 | 2.04 | 1.72 |
| 16.00 | 2.08 | 3.40 | 1.93 | 3.08 |
| 24.00 | 0.71 | 0.20 | 0.72 | 0.19 |
| 48.00 | 0.21 | 0.04 | 0.21 | 0.08 |
| 72.00 | 0.15 | 0.02 | 0.14 | 0.02 |

The results in Table 7 illustrates that the AUC and Cmax ratios for Modafinil tablets of the invention versus PROVIGIL® 200 are well within the bioequivalence acceptance criteria.

TABLE 7

Pharmacokinetic parameters

| Bioequivalence Parameters | Point Estimate Test/Reference | Lower Confidence | Upper Confidence |
|---|---|---|---|
| $C_{max}$ | 97.75 | 92.59 | 103.19 |
| $AUC_{0-t}$ | 98.41 | 91.52 | 105.81 |
| $AUC_{0-\infty}$ | 99.96 | 94.84 | 105.36 |

What is claimed is:

1. An oral pharmaceutical composition prepared by a method comprising double compacting modafinil particles and one or more pharmaceutically acceptable excipients, wherein the double compacted modafinil particles have a size distribution such that at least about 65% of the modafinil particles have a diameter greater than about 220 microns, wherein the modafinil particles comprise about 20-50% by weight of the composition, and wherein the pharmaceutical composition releases about 75% modafinil within 10 minutes.

2. The pharmaceutical composition of claim 1, wherein the double compaction method comprises the steps of:
   (i) blending modafinil particles and one or more pharmaceutically acceptable excipients to form a mixture;
   (ii) subjecting the mixture of step (i) to compression to form a first slug;
   (iii) sizing the granules by passing through a 1 mm size screen;
   (iv) blending the granules from step (iii) with one or more pharmaceutically acceptable excipients to form a second mixture;
   (v) subjecting the mixture of step (iv) to compression to form a second slug;
   (vi) sizing the granules by passing through a 1 mm sized screen;
   (vii) blending the granules from step (vi) with one or more pharmaceutically acceptable excipients; and
   (viii) compressing the mixture of step (vii) into a tablet.

3. The pharmaceutical composition of claim 2, wherein the first slug comprises modafinil, hydroxypropylcellulose, pregelatinized starch, first portions of lactose monohydrate, talc, and sodium lauryl sulphate.

4. The pharmaceutical composition of claim 2, wherein the second slug comprises granules from step (iii) and lactose monohydrate, talc, sodium lauryl sulphate, crospovidone, sodium stearyl fumarate, and mixtures thereof.

5. The pharmaceutical composition of claim 1, wherein the one or more pharmaceutically acceptable excipients are dissolution enhancing excipients.

6. The pharmaceutical composition of claim 1, wherein the one or more pharmaceutically acceptable excipients comprise binders, diluents, disintegrants, surfactants, lubricants, glidants, and coloring agents.

7. The pharmaceutical composition of claim 6, wherein the binder is selected from the group consisting of hydroxypropyl cellulose and cellulose derivatives, polyvidone, polyvinyl pyrrolidone, gelatin, natural gums, starch paste, pre-gelatinized starch, sucrose, corn syrup, polyethylene glycols and sodium alginate, ammonium calcium alginate, magnesium aluminum silicate, polyethylene glycols, and mixtures thereof.

8. The pharmaceutical composition of claim 7, wherein the binder is hydroxypropyl cellulose.

9. The pharmaceutical composition of claim 6, wherein the disintegrant is selected from the group consisting of starch and starch derivatives, pre-gelatinized starch, sodium starch glycolate, cross-linked sodium carboxymethyl cellulose, crospovidone and cross-linked polyvinylpyrrolidone, microcrystalline cellulose and mixtures thereof.

10. The pharmaceutical composition of claim 9, wherein the disintegrant is crospovidone or pre-gelatinized starch.

11. The pharmaceutical composition of claim 6, wherein the lubricant is selected from the group consisting of vegetable oils, polyethylene glycols, stearic acid, sodium steryl fumarate and salts of stearic acid, talc and mineral salts, organic salts, polyvinyl alcohols, and mixtures thereof.

12. The pharmaceutical composition claim 11, wherein the lubricant is sodium stearyl fumarate, or talc.

13. The pharmaceutical composition of claim 6, wherein the diluent is selected from the group consisting of spray-dried or anhydrous lactose monohydrate, sucrose, dextrose, starch, pre-gelatinized starch, polyols, cellulose, inorganic salts, and mixtures thereof.

14. The pharmaceutical composition of claim 13, wherein the diluent is lactose monohydrate.

15. The pharmaceutical composition of claim 6, wherein the surfactant comprises one or more anionic surfactants.

16. The pharmaceutical composition of claim 15, wherein the anionic surfactant is selected from the group consisting of sodium lauryl sulphate, sodium laurate, dialkyl sodium sulfosuccinates, sodium stearate, potassium stearate, and sodium oleate.

17. The pharmaceutical composition of claim 16, wherein the anionic surfactant is sodium lauryl sulphate.

18. The pharmaceutical composition of claim 1, wherein the pharmaceutical composition releases about 94% modafinil within 30 minutes.

19. The pharmaceutical composition of claim 1, wherein the pharmaceutical composition comprises about 100 or 200 milligrams of modafinil.

* * * * *